United States Patent
Moshe

(10) Patent No.: US 12,092,569 B2
(45) Date of Patent: Sep. 17, 2024

(54) METHOD AND SYSTEM FOR DETECTING A BIOLOGICAL SUBSTANCE BY HYPERSPECTRAL IMAGING

(71) Applicant: Green Vision Systems Ltd., Tel-Aviv (IL)

(72) Inventor: Danny S. Moshe, Ramat-HaSharon (IL)

(73) Assignee: Green Vision Systems Ltd., Tel Aviv (IL)

( * ) Notice: Subject to any disclaimer, the term of this patent is extended or adjusted under 35 U.S.C. 154(b) by 0 days.

(21) Appl. No.: 17/506,762

(22) Filed: Oct. 21, 2021

(65) Prior Publication Data

US 2022/0120674 A1   Apr. 21, 2022

Related U.S. Application Data

(60) Provisional application No. 63/184,319, filed on May 5, 2021, provisional application No. 63/094,391, filed on Oct. 21, 2020.

(51) Int. Cl.

| | |
|---|---|
| *G01N 21/31* | (2006.01) |
| *G01N 1/44* | (2006.01) |
| *G01N 33/497* | (2006.01) |
| *G06K 9/00* | (2022.01) |
| *G06K 9/46* | (2006.01) |
| *G06V 10/58* | (2022.01) |
| *G06V 10/60* | (2022.01) |
| *G06V 20/69* | (2022.01) |
| *A61B 5/097* | (2006.01) |

(52) U.S. Cl.
CPC ............... *G01N 21/31* (2013.01); *G01N 1/44* (2013.01); *G01N 33/497* (2013.01); *G06V 10/58* (2022.01); *G06V 10/60* (2022.01); *G06V 20/693* (2022.01); *A61B 5/097* (2013.01); *G06V 2201/03* (2022.01)

(58) Field of Classification Search
CPC ........ G01N 21/31; G01N 1/44; G01N 33/497; G06V 10/60; G06V 20/693; G06K 9/00134

See application file for complete search history.

(56) References Cited

U.S. PATENT DOCUMENTS

| | | |
|---|---|---|
| 8,159,661 B2 | 4/2012 | Moshe et al. |
| 8,953,158 B2 | 2/2015 | Moshe et al. |
| 10,317,571 B2 | 6/2019 | Moshe |

(Continued)

FOREIGN PATENT DOCUMENTS

| | | |
|---|---|---|
| WO | WO 2012/150557 | 11/2012 |
| WO | WO 2016/087589 | 6/2016 |

OTHER PUBLICATIONS

Hyperspectral imaging using the single-pixel Fourier transform technique Senlin Jin, Wangwei Hui, Yunlong Wang, Kaicheng Huang, Quishuai Shi, Cuifeng Ying, Dongqi Liu, Qing Ye, Wenyuan Zhou, Jianguo Tian Nature Scientific Reports Mar. 24, 2017 (Year: 2017).*

(Continued)

*Primary Examiner* — Brian R Gordon
*Assistant Examiner* — Dwan A Gerido

(57) ABSTRACT

A method of detecting a biological substance in a sample, comprises: illuminate the sample by light; imaging the illuminated sample by Fourier transform hyperspectral imaging; and analyzing the obtained hyperspectral image to detect the biological substance in a sample.

13 Claims, 7 Drawing Sheets

(56) References Cited

U.S. PATENT DOCUMENTS

| | | | |
|---|---|---|---|
| 2010/0028859 A1* | 2/2010 | S. Moshe | G01N 33/569 |
| | | | 435/7.1 |
| 2010/0056928 A1* | 3/2010 | Zuzak | G01J 3/2823 |
| | | | 356/302 |
| 2012/0202192 A1* | 8/2012 | Moshe | G01N 21/6428 |
| | | | 435/5 |
| 2013/0195328 A1 | 8/2013 | Tanji | |
| 2014/0327760 A1* | 11/2014 | Kurz | G01V 99/00 |
| | | | 348/135 |
| 2016/0011103 A1* | 1/2016 | Morishima | G01N 21/3577 |
| | | | 435/165 |
| 2018/0107857 A1 | 4/2018 | Dante et al. | |
| 2019/0056297 A1 | 2/2019 | Hoyt | |

OTHER PUBLICATIONS

Patents Act 1977: Patents Rules 2007, Report under Section 15A Dated Nov. 1, 2021 From the Intellectual Property Office of the United Kingdom of Great Britain Re. Application No. 2115094.1. (5 Pages).

Patents Act 1977: Combined Search and Examination Report Under Sections 17 and 18(3) Dated Mar. 11, 2022 From the Intellectual Property Office of the United Kingdom of Great Britain Re. Application No. 2115094.1. (8 Pages).

Patents Act 1977: Examination Report Under Sections 18(3) Dated Mar. 30, 2023 From the Intellectual Property Office of the United Kingdom of Great Britain Re. Application No. 2115094.1. (5 Pages).

\* cited by examiner

HyperEye Matush vs. HyperEye Saliva
y=2.9246x+0.902
$R^2$=0.8005 example: HSI image from NGT person, saliva sample mixed with GVS' reagents example: HSI image from PST person, saliva sample mixed with GVS' reagents

METHOD AND SYSTEM FOR DETECTING A BIOLOGICAL SUBSTANCE BY HYPERSPECTRAL IMAGING

RELATED APPLICATIONS

This application claims the benefit of priority under 35 USC § 119(e) of U.S. Provisional Patent Application Nos. 63/094,391 filed on Oct. 21, 2020, and 63/184,319 filed on May 5, 2021.

This application is also related to co-filed Israel and Great Britain Patent Applications, having the same title as the instant application.

The contents of the above applications are all incorporated by reference as if fully set forth herein in their entirety.

FIELD AND BACKGROUND OF THE INVENTION

The present invention, in some embodiments thereof, relates to detection and, more particularly, but not exclusively, to a method and system for detecting a substance, optionally and preferably a biological substance, by hyperspectral imaging.

Infectious diseases are caused by a pathogenic microorganism, like a virus, bacterium, fungus, or the like which enters and propagates in a living body. In particular, diseases caused by pathogenic viruses are of increasing concern to health authorities. Prominent recent examples are the outbreaks of diseases caused by the SARS and MERS coronaviruses (SARS-CoV-2, MERS-CoV), the avian influenza virus (AIV), Ebola virus (EBOV) and the virus responsible for COVID19 (SARS-CoV-2). With increasing globalization, the threat of diseases caused by such highly pathogenic viruses has been amplified.

For example, SARS-CoV-2 (causing a respiratory illness known as COVID-19) claimed many thousands of lives long before any vaccine was available. Less than 3 months after first detection, the World Health Organization ("WHO") declared SARS-CoV-2 a Public Health Emergency of International concern, and less than 4 months after the first detection, the WHO declared it a global pandemic. By Apr. 8, 2020, over 1.5 million people had been infected, with over 88,000 deaths. Death rates varied widely by country for a wide range of factors, such as how early in the outbreak quarantine and social distancing measures were put into effect, the average age of the population, the availability of medical facilities, cultural norms related to human contact, and many other factors.

U.S. Pat. No. 8,159,661, the contents of which are hereby incorporated by reference, discloses a method for hyperspectral imaging and analysis of a sample of matter, for identifying and characterizing an object of interest therein. U.S. Pat. No. 8,953,158, the contents of which are hereby incorporated by reference discloses a system for grading an agricultural product employing hyperspectral imaging and analysis. U.S. Pat. No. 10,317,571, the contents of which are hereby incorporated by reference, discloses a technique for monitoring contaminated outdoor air particulate matter throughout a region, via hyperspectral imaging and analysis. WO2012150557, the contents of which are hereby incorporated by reference, discloses a microelectromechanical system (MEMS) for hyperspectral imaging and analysis. The system is applicable for on line or off-line hyperspectral imaging and analyzing, on a miniaturized scale.

SUMMARY OF THE INVENTION

According to some embodiments of the invention the present invention there is provided a method of detecting a biological substance in a sample. The method comprises: illuminate the sample by light; imaging the illuminated sample by hyperspectral imaging a plurality of times, to generate a plurality of hyperspectral images; accessing a computer readable medium containing a library of hyperspectral signatures; and analyzing the plurality of hyperspectral images using the library to detect the biological substance in a sample.

According to an aspect of some embodiments of the present invention there is provided a method of detecting a biological substance in a sample. The method comprises: illuminate the sample by light; imaging the illuminated sample by hyperspectral imaging a plurality of times, to generate a plurality of hyperspectral images; accessing a computer readable medium storing a machine learning procedure trained for predicting presence of a hyperspectral signature of the biological substance in hyperspectral images; feeding the procedure with the plurality of hyperspectral images; and receiving from the procedure an output indicative of a likelihood that the hyperspectral images contains the hyperspectral signature of the substance, thereby detecting the biological substance in the sample.

According to some embodiments of the invention the at least two Fourier transform hyperspectral images are acquired from two different view points with respect to the sample.

According to some embodiments of the invention the method comprises adding to the sample a bio-marker that directly or indirectly binds to the substance, wherein the library comprises hyperspectral signatures of bio-markers.

According to some embodiments of the invention the method comprises collecting the sample as aerosol.

According to some embodiments of the invention the collecting is from a mammalian subject.

According to some embodiments of the invention the collecting comprises collecting an environmental air.

According to some embodiments of the invention the method comprises collecting the sample from a plant.

According to some embodiments of the invention the method comprises applying a thermal treatment to the sample prior to the imaging.

According to some embodiments of the invention the substance is a virus. According to some embodiments of the invention the virus is an airborne virus.

According to some embodiments of the invention the substance is a fungus.

According to some embodiments of the invention the substance is a bacterium.

According to some embodiments of the invention the method comprises estimating a level of the biological substance in the sample.

According to an aspect of some embodiments of the present invention there is provided a system for detecting a biological substance in a sample. The system comprises: a light source configured for illuminating the sample by light; a hyperspectral imaging system configured for imaging the illuminated sample by Fourier transform hyperspectral imaging; a controller, configured for controlling the hyperspectral imaging system to acquire a plurality of hyperspectral images; an image processor, configured for processing the plurality of hyperspectral images to identify a hyperspectral signature of the biological substance in the hyperspectral images.

According to some embodiments of the invention the image processor is configured for accessing a computer readable medium containing a library of hyperspectral signatures, wherein the identification of the hyperspectral signature is based on the hyperspectral signatures in the library.

According to some embodiments of the invention the image processor is configured to access a computer readable medium storing a machine learning procedure trained for predicting presence of a hyperspectral signature of a biological substance in hyperspectral images, to feed the procedure with the plurality of hyperspectral images, and to generate by the procedure output indicative of a likelihood that the hyperspectral images contains the hyperspectral signature of the substance.

According to some embodiments of the invention the controller is configured to control the hyperspectral imaging system to acquire at least two hyperspectral images from two different view points with respect to the sample.

According to some embodiments of the invention the system comprises a heating system configured to apply a thermal treatment to the sample prior to the imaging.

According to some embodiments of the invention the image processor is configured to estimate a level of the biological substance in the sample, based on a distribution of the hyperspectral signature in the hyperspectral images.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
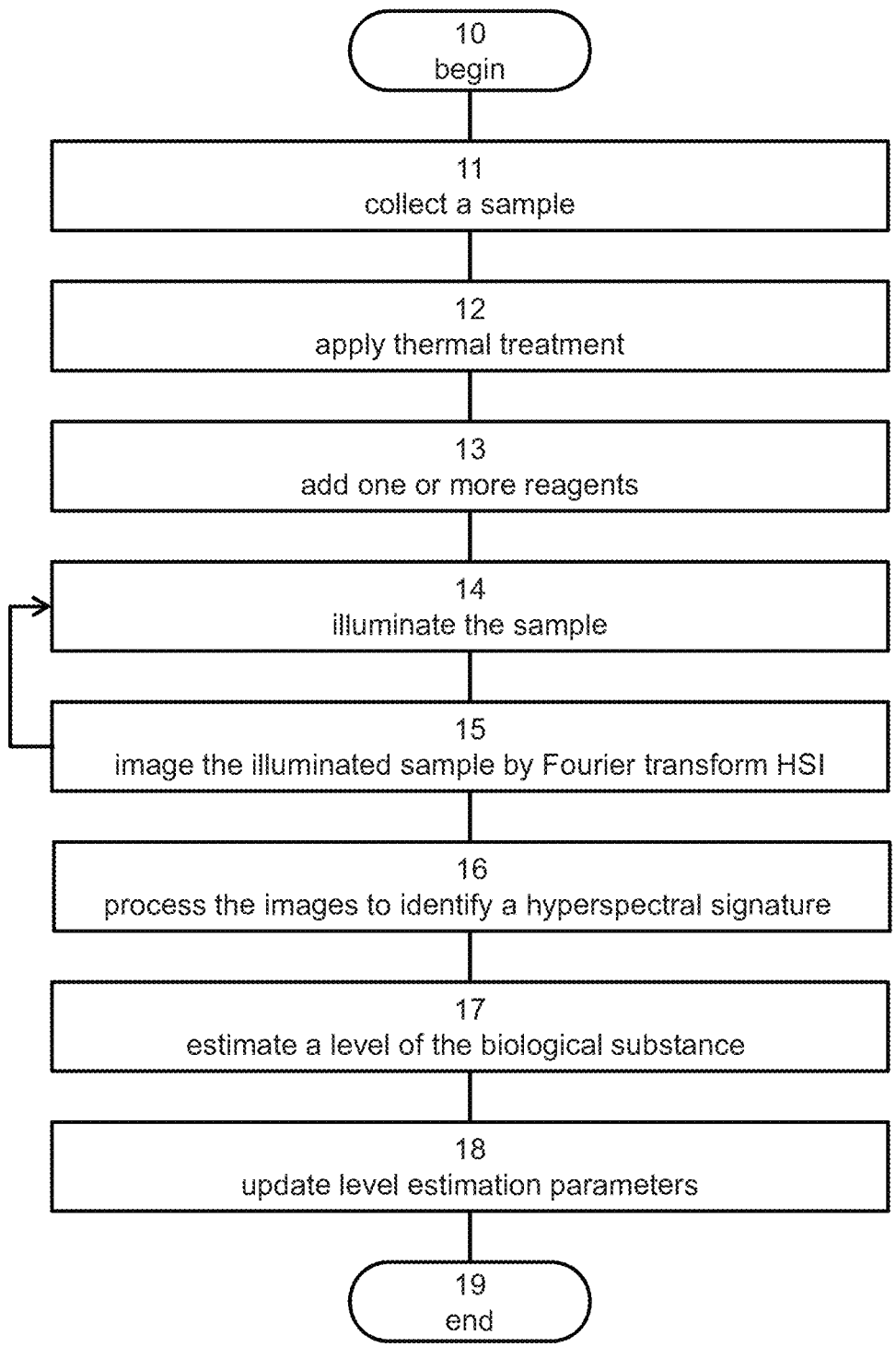
FIG. 1 is a flowchart diagram of the method according to various exemplary embodiments of the present invention.

The present invention, in some embodiments thereof, relates to detection and, more particularly, but not exclusively, to a method and system for detecting a substance, optionally and preferably a biological substance, by hyperspectral imaging.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The leading analytical chemistry technologies currently available include PCR, immunoassay, basic microscopy, Fourier Transform Infrared (FTIR), and Raman Laser Spectroscopy (RLS). These methods require sample collection followed by laboratory analysis. The approaches are effective but have limitations in time, cost, and labor. Further, they can only detect bio-aerosols they are designed to classify, and are unable to identify anomalies that could be potential threats. Both Polymerase Chain Reaction (PCR) and RAMAN high-end high-performances techniques are recognized as the most reliable laboratory techniques, along with culture methods. Current PCR methods require sample preparation to remove inhibitors from the sample that may result in a false negative and add reagents necessary to run PCR. This sample processing requires significant laboratory operations, a job unqualified personnel cannot perform. The Raman technology works well for laboratory use but is less reliable outside of the laboratory. This is because the conditions in the lab (light, temperature, background etc.) are optimized and the signal is sufficiently strong.

The present embodiments describe a technique for detecting a biological substance in a sample by Fourier transform hyperspectral imaging. The technique can, in some embodiments of the present invention provides a near real time (e.g., within less than an hour, or less than 45 minutes or less than 30 minutes, or less than 15 minutes, for example, within 10 minutes or less) detection of high volume of air.

The biological substance can be of any type, such as, but not limited to, a virus, a bacterium, and a fungus. Of particular interest is a case in which the biological substance to be identified is a virus, optionally and preferably an airborne virus.

Representative examples of viruses that are contemplates in accordance with some embodiments of the present invention include one or more species of the following families Adenoviridae, Arenaviridae, Astroviridae, Bunyaviridae, Caliciviridae, Coronaviridae, Filoviridae, Flaviviridae, Hepadnaviridae, Hepeviridae, Herpesviridae, Orthomyxoviridae, Papillomaviridae, Paramyxoviridae, Parvoviridae, Picornaviridae, Polyomaviridae, Poxviridae, Reoviridae, Retroviridae, Rhabdoviridae, and Togaviridae.

According to embodiments of the present invention, the virus is selected from the group consisting of Adenovirus, Bocavirus, Coronavirus, Enterovirus, Influenza virus, Metapneumovirus, Parainfluenza virus, Respiratory syncytial virus and Rhinovirus. According to embodiments of the present invention, the coronavirus is severe acute respiratory syndrome coronavirus (SARS-CoV-2) or Middle East respiratory syndrome coronavirus (MERS-CoV). According to embodiments of the present invention, the coronavirus is SARS-CoV-2. According to a specific embodiment, the virus is Human metapneumovirus, Bocavirus or Enterovirus.

For specific biological substance, for example, a virus, an additional reagent (such as, but not limited to, an antibody), can be added to the sample. Following mixing, few drops of the sample is imaged, using a Fourier Transform hyperspectral imaging system equipped with a high performance microscope (e.g., about 0.25 micron per pixel or less) and optics.

At least part of the operations described herein can be implemented by a data processor having image processing capabilities, e.g., a dedicated circuitry or a general purpose computer, configured for receiving data and executing the operations described below. At least part of the operations can be implemented by a cloud-computing facility at a remote location based on a repeatedly updated database of hyperspectral signatures obtained from hyperspectral images collected on site.

Computer programs implementing the method of the present embodiments can commonly be distributed to users by a communication network or on a distribution medium such as, but not limited to, a flash memory device and a portable hard drive.

From the communication network or distribution medium, the computer programs can be copied to a hard disk or a similar intermediate storage medium. The computer programs can be run by loading the code instructions either from their distribution medium or their intermediate storage medium into the execution memory of the computer, configuring the computer to act in accordance with the method of this invention. During operation, the computer can store in a memory data structures or values obtained by intermediate calculations and pulls these data structures or values for use in subsequent operation. All these operations are well-known to those skilled in the art of computer systems.

Processing operations described herein may be performed by means of processer circuit, such as a DSP, microcontroller, FPGA, ASIC, etc., or any other conventional and/or dedicated computing system.

The method of the present embodiments can be embodied in many forms. For example, it can be embodied in on a tangible medium such as a computer for performing the method operations. It can be embodied on a computer readable medium, comprising computer readable instructions for carrying out the method operations. In can also be embodied in electronic device having digital computer capabilities arranged to run the computer program on the tangible medium or execute the instruction on a computer readable medium.

Referring now to the drawings, FIG. 1 is a flowchart diagram of the method according to various exemplary embodiments of the present invention. It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

The method begins at 10 and optionally and preferably continues to 11 at which a sample is collected. The sample is preferably collected as an aerosol, but collecting a liquid sample is also contemplated. The sample can be collected from a living subject (e.g., a mammalian subject) or a plant, or it can be collected from an environmental air. When the sample is collected as an aerosol, it can be collected using an air filter positioned at a location in the environment or in proximity to a living subject. For example, a breath detection device can be used as a collector for aerosol produced by the subject. When the sample is collected as a liquid, it can be collected as a sampling swab or the like. The sample can be collected from an indoor source of air (e.g., a post office, an airport, a subway station, a shopping mall, a sports arena, an office building, closed room, school, medical center, etc.), or from an outdoor source of air.

The environmental air indoor typically includes numerous, spatially or/and temporally variable different types and concentrations of background components, such as dust (fine, dry particles of matter), pollen (fine particulate or powder-like material consisting of pollen grains produced by plants), minerals, and chemical matter. Such background components in the air source can be in aerosol form, being a gaseous suspension of fine solid or liquid particles which circulate throughout the air.

The method optionally continues to 12 at which a thermal treatment is applied to the sample. The thermal treatment is optionally and preferably selected to (i) reduce the bio contamination risks for the operator, and/or (ii) reduce humidity, for example, when sampling form indoor and/or outdoor air that might affect the analysis. In some embodiments of the present invention the method proceeds to 13 at which one or more reagents (e.g., background reducing reagents, separation reagents, activation reagents, buffer reagents) to the sample. The addition of reagents is optionally and preferably followed by stirring and or vibrating the sample for better mixing).

The present embodiments contemplate one or more of many types of reagents. In some embodiments of the present invention the reagent is or comprises an antibody that is specific to the biological substance to be detected. The antibody can be monoclonal, polyclonal, chimeric, or a fragment of the foregoing. A representative example of an antibody suitable for some embodiments of the present invention, includes, without limitation, Anti-Coronavirus spike Antibody (e.g., 40592-T62 manufactured by Sino Biological).

Suitable sources for antibodies include commercially available sources such as, for example, Abazyme, Abnova, AssayPro, Affinity Biologicals, AntibodyShop, Aviva bioscience, Biogenesis, Biosense Laboratories, Calbiochem, Cell Sciences, Chemicon International, Chemokine, Clontech, Cytolab, DAKO, Diagnostic BioSystems, eBioscience, Endocrine Technologies, Enzo Biochem, Eurogentec, Fusion Antibodies, Genesis Biotech, GloboZymes, Haematologic Technologies, Immunodetect, Immunodiagnostik, Immunometrics, Immunostar, Immunovision, Biogenex, Invitrogen, Jackson ImmunoResearch Laboratory, KMI Diagnostics, Koma Biotech, LabFrontier Life Science Institute, Lee Laboratories, Lifescreen, Maine Biotechnology Services, Mediclone, MicroPharm Ltd., ModiQuest, Molecular Innovations, Molecular Probes, Neoclone, Neuromics, New England Biolabs, Novocastra, Novus Biologicals, Oncogene Research Products, Orbigen, Oxford Biotechnology, Panvera, PerkinElmer Life Sciences, Pharmingen, Phoenix Pharmaceuticals, Pierce Chemical Company, Polymun Scientific, Polysiences, Inc., Promega Corporation, Proteogenix, Protos Immunoresearch, QED Biosciences, Inc., R&D Systems, Repligen, Research Diagnostics, Roboscreen, Santa Cruz Biotechnology, Seikagaku America, Serological Corporation, Serotec, SigmaAldrich, StemCell Technologies, Synaptic Systems GmbH, Technopharm, Terra Nova Biotechnology, TiterMax, Trillium Diagnostics, Upstate Biotechnology, US Biological, Vector Laboratories, Wako Pure Chemical Industries, and Zeptometrix. However, for a given the biological substance to be detected, the skilled artisan can routinely make antibodies specific to that biological substance.

In some embodiments, the reagent is, or comprise, a spectral marker that is specific to the biological substance to be detected or to the antibody (if employed). The spectral marker is preferably a marker that has a hyperspectral signature that is identifiable via hyperspectral imaging, and optionally and preferably a hyperspectral signature that is probabilistically unique (namely that the probability of finding a marker having the same hyperspectral signature is less than a predetermined threshold, e.g., less than 0.001). The spectral marker can be a chemical type of spectral marker, or a biological type of spectral marker. The chemical or biological spectral marker forms with the biological substance, optionally and preferably via the antibody, a complex which exhibits a detectable and identifiable cluster of hyperspectral signatures.

The method continues to 14 at which the sample is illuminated by light. The light can be a broadband light in which case the light is dispersed following the interaction with the sample, or, alternatively, the light can have a specific central wavelength and a relatively narrow width (e.g., less than 50 nm or less than 40 nm or less than 30 nm, for example, 20 nm or less), in which case the method employs spectral scanning during the illumination. The sample can be illuminated from a specific direction or, more preferably, from multiple directions. When the sample is illuminated from multiple directions the illumination is preferably simultaneous from all the directions.

In any of the above embodiments, the illumination is effective to provide spectral information over a range selected based on the biological substance to be detected and/or on the spectral marker added at 13 (in embodiments in which it is employed). Representative examples of wavelengths ranges suitable for the present embodiments include, without limitation, from about 380 nm to about 500 nm, or from about 450 nm to about 700 nm, or from about 500 nm to about 900 nm, or from about 850 nm to about 1300 nm, or from about 1100 nm to about 1650 nm, or from about 2000 nm to about 2350 nm, or from about 3000 to about 4000 nm. Other wavelengths ranges are also contemplated in some embodiments of the present invention.

At 15 the illuminated sample is imaged by a Fourier Transform hyperspectral imaging system equipped with a high performance microscope (e.g., about 0.25 micron per pixel or less) and dedicated optics. Fourier Transform hyperspectral imaging is a technique in which the spectrum at each pixel of the image is obtained by Fourier Transform. It was unexpectedly found by the Inventor that Fourier Transform hyperspectral imaging allows the detection of submicrometric objects, such as, but not limited to, viruses.

When Fourier Transform hyperspectral imaging is employed, the spectral scanning employed at 14 is optionally and preferably an optical path difference scanning. For example, two light beams of the illumination light can be guided through different optical paths, and one or both of these different optical paths can be varied, continuously or in steps, such that the optical path difference between the two paths is varied, thus storing in each pixel, data corresponding to a plurality of different optical signals from the sample. Since the optical path difference correlates with the propagation time of the light beams, the Fourier transform of the data stored in a given pixel transforms the data to the wavelength domain or, equivalently, the frequency domain, thus providing an optical spectrum for that pixel.

Preferably, operations 14 and 15 are executed a plurality of times (e.g., 10 or more, more preferably 20 or more, more preferably 30 or more times), to generate a plurality of hyperspectral images. In some embodiments of the present invention the images are acquired from a plurality of viewpoints relative to the sample, and in some embodiments of the present invention each of the images is acquired from a different region of the sample (e.g., to provide a mosaic of hyperspectral images).

The number of hyperspectral images that are acquired per sample is optionally and preferably selected based on the expected concentration of the biological substance. For example, suppose that the biological substance is likely to cause a particular disease, e.g., a virus. Then, when the source of the sample is a subject having symptoms that may be indicative of the disease, the concentration of the biological substance is expected to be high, and when the source of the sample is an asymptomatic subject, the concentration of the biological substance is expected to be low. Another case in which the concentration of the biological substance is expected to be low is when the sample is collected from the environment and not from a specific subject. The number of hyperspectral images that are acquired at 15 is smaller in cases in which the concentration is expected to be high than in cases in which the concentration is expected to be low. A typical number of hyperspectral images for a sample having a size of a few milliliters (e.g., from about 6 milliliters to about 12 milliliters) is from about 10 hyperspectral images to about 30 hyperspectral images.

A Fourier transform hyperspectral image can be viewed as a 3D array of data that combines spectral information (e.g., wavelength $\lambda$) with spatial organization (e.g., x-y locations on a rectangular grid). The hyperspectral image is thus a data structure that provides a spectrum for each picture-element (e.g., a pixel) of the image. A hyperspectral image allows the extraction of features and the evaluation of quantities that are difficult, and in some cases even impossible, to obtain otherwise. The spectrum in each picture-element is preferably digitized at a resolution of 10 nm or less, more preferably 8 nm or less, more preferably 6 nm or less, more preferably 4 nm or less, more preferably 2 nm or less. The digitized spectrum can be provided in the form of a set of intensity values, each corresponding to a different wavelength.

Operations 14 and 15 can be executed using any hyperspectral imaging system known in the art. Representative examples include, without limitation, the hyperspectral imaging systems disclosed in U.S. Pat. No. 7,411,682, and WO2012150557, the contents of which are hereby incorporated by reference. Commercially available Fourier transform hyperspectral imaging systems suitable for the present embodiments are marketed under the trade name Hyper-Eye® by Green Vision Systems Ltd., Tel Aviv, Israel. Operations 14 and 15 can be executed either indoor or in an outdoor environment.

The method continues to 16 at which the hyperspectral images are processed to identify a hyperspectral signature of the biological substance (or the hyperspectral signature of the spectral marker, when employed) in the hyperspectral images.

In the simplest case, the hyperspectral signature is a spectrum, namely a set of intensity values, one value for each of a respective set of wavelengths. A more complex hyperspectral signature, which is also contemplated according to some embodiments of the present invention, is a set of a plurality of spectra, each associated with a spatial location over a grid, e.g., a rectangular grid. Such a complex hyperspectral signature can be represented by a hyperspectral image.

In some embodiments of the present invention the hyperspectral images are also processed to identify reference hyperspectral signatures in the hyperspectral images. Reference hyperspectral signatures can be, for example, hyperspectral signatures of a sample that is collected in a similar manner but that is devoid of the biological substance to be detected. The inventor found that identification of reference hyperspectral signatures significantly improve the sensitivity and accuracy of the technique.

The hyperspectral signature can be identified in more than one way.

In some embodiments of the present invention a computer readable medium containing a library of hyperspectral signatures or a library of clusters of hyperspectral signatures, is accessed. The library can include a plurality of entries each including a hyperspectral signature or a library cluster of hyperspectral signatures and a corresponding biological substance or corresponding spectral marker(s).

The method can access the library and it search for a library hyperspectral signature, or a library cluster of hyperspectral signatures, that best matches the data in the acquired hyperspectral image. The method can then pull the corresponding biological substance from the library and determine that the sample contains that biological substance. The search and comparison is optionally and preferably executed separately for each of the hyperspectral images. For each image, the search and comparison can be done separately for each pixel of the image, or collectively for groups of pixels forming a region over the image.

In some embodiments of the present invention a machine learning procedure is employed.

As used herein the term "machine learning" refers to a procedure embodied as a computer program configured to induce patterns, regularities, or rules from previously collected data to develop an appropriate response to future data, or describe the data in some meaningful way.

Use of machine learning is particularly, but not exclusively, advantageous when the dataset includes multidimensional entries.

In machine learning, information can be acquired via supervised learning or unsupervised learning. In some embodiments of the invention the machine learning procedure comprises, or is, a supervised learning procedure. In supervised learning, global or local goal functions are used to optimize the structure of the learning system. In other words, in supervised learning there is a desired response, which is used by the system to guide the learning.

In some embodiments of the invention the machine learning procedure comprises, or is, an unsupervised learning procedure. In unsupervised learning there are typically no goal functions. In particular, the learning system is not provided with a set of rules. One form of unsupervised learning according to some embodiments of the present invention is unsupervised clustering (e.g. backgrounds and targets spectral signatures and special characteristics) in which the data objects are not class labeled, a priori.

Representative examples of machine learning procedures suitable for the present embodiments, including, without limitation, clustering, association rule algorithms, feature evaluation algorithms, subset selection algorithms, support vector machines, classification rules, cost-sensitive classifiers, vote algorithms, stacking algorithms, Bayesian networks, decision trees, neural networks, instance-based algorithms, linear modeling algorithms, k-nearest neighbors analysis, ensemble learning algorithms, probabilistic models, graphical models, logistic regression methods (including multinomial logistic regression methods), gradient ascent methods, singular value decomposition methods and principle component analysis. Among neural network models, the self-organizing map and adaptive resonance theory are commonly used unsupervised learning algorithms. The adaptive resonance theory model allows the number of clusters to vary with problem size and lets the user control the degree of similarity between members of the same clusters by means of a user-defined constant called the vigilance parameter.

Following is an overview of some machine learning procedures suitable for the present embodiments.

Association rule algorithm is a technique for extracting meaningful association patterns among features.

The term "association", in the context of machine learning, refers to any interrelation among features, not just ones that predict a particular class or numeric value. Association includes, but it is not limited to, finding association rules, finding patterns, performing feature evaluation, performing feature subset selection, developing predictive models, and understanding interactions between features.

The term "association rules" refers to elements that co-occur frequently within the datasets. It includes, but is not limited to association patterns, discriminative patterns, frequent patterns, closed patterns, and colossal patterns.

A usual primary step of association rule algorithm is to find a set of items or features that are most frequent among all the observations. Once the list is obtained, rules can be extracted from them.

The aforementioned self-organizing map is an unsupervised learning technique often used for visualization and analysis of high-dimensional data. Typical applications are focused on the visualization of the central dependencies within the data on the map. The map generated by the algorithm can be used to speed up the identification of association rules by other algorithms. The algorithm typically includes a grid of processing units, referred to as "neurons". Each neuron is associated with a feature vector referred to as observation. The map attempts to represent all the available observations with optimal accuracy using a restricted set of models. At the same time the models become ordered on the grid so that similar models are close to each other and dissimilar models far from each other. This procedure enables the identification as well as the visualization of dependencies or associations between the features in the data.

Feature evaluation algorithms are directed to the ranking of features or to the ranking followed by the selection of features based on their impact.

The term "feature" in the context of machine learning refers to one or more raw input variables, to one or more processed variables, or to one or more mathematical combinations of other variables, including raw variables and processed variables. Features may be continuous or discrete.

Information gain is one of the machine learning methods suitable for feature evaluation. The definition of information gain requires the definition of entropy, which is a measure of impurity in a collection of training instances. The reduction in entropy of the target feature that occurs by knowing the values of a certain feature is called information gain. Information gain may be used as a parameter to determine the effectiveness of a feature in explaining the type of biological substance. Symmetrical uncertainty is an algorithm that can be used by a feature selection algorithm, according to some embodiments of the present invention. Symmetrical uncertainty compensates for information gain's bias towards features with more values by normalizing features to a [0,1] range.

Subset selection algorithms rely on a combination of an evaluation algorithm and a search algorithm. Similarly to feature evaluation algorithms, subset selection algorithms rank subsets of features. Unlike feature evaluation algorithms, however, a subset selection algorithm suitable for the present embodiments aims at selecting the subset of features with the highest impact on the type of biological substance, while accounting for the degree of redundancy between the features included in the subset. The benefits from feature subset selection include facilitating data visualization and understanding, reducing measurement and storage requirements, reducing training and utilization times, and eliminating distracting features to improve classification.

Two basic approaches to subset selection algorithms are the process of adding features to a working subset (forward selection) and deleting from the current subset of features (backward elimination). In machine learning, forward selection is done differently than the statistical procedure with the same name. The feature to be added to the current subset in machine learning is found by evaluating the performance of the current subset augmented by one new feature using cross-validation. In forward selection, subsets are built up by adding each remaining feature in turn to the current subset while evaluating the expected performance of each new subset using cross-validation. The feature that leads to the best performance when added to the current subset is retained and the process continues. The search ends when none of the remaining available features improves the predictive ability of the current subset. This process finds a local optimum set of features.

Backward elimination is implemented in a similar fashion. With backward elimination, the search ends when further reduction in the feature set does not improve the predictive ability of the subset. The present embodiments contemplate search algorithms that search forward, backward or in both directions. Representative examples of search algorithms suitable for the present embodiments include, without limitation, exhaustive search, greedy hill-climbing, random perturbations of subsets, wrapper algorithms, probabilistic race search, schemata search, rank race search, and Bayesian classifier.

A decision tree is a decision support algorithm that forms a logical pathway of steps involved in considering the input to make a decision.

The term "decision tree" refers to any type of tree-based learning algorithms, including, but not limited to, model trees, classification trees, and regression trees.

A decision tree can be used to classify the datasets or their relation hierarchically. The decision tree has tree structure that includes branch nodes and leaf nodes. Each branch node specifies an attribute (splitting attribute) and a test (splitting test) to be carried out on the value of the splitting attribute, and branches out to other nodes for all possible outcomes of the splitting test. The branch node that is the root of the decision tree is called the root node. Each leaf node can represent a classification (e.g., whether a particular portion of the group dataset matches a particular portion of the subject-specific dataset) or a value. The leaf nodes can also contain additional information about the represented classification such as a confidence score that measures a confidence in the represented classification (i.e., the likelihood of the classification being accurate). For example, the confidence score can be a continuous value ranging from 0 to 1, which a score of 0 indicating a very low confidence (e.g., the indication value of the represented classification is very low) and a score of 1 indicating a very high confidence (e.g., the represented classification is almost certainly accurate).

Support vector machines are algorithms that are based on statistical learning theory. A support vector machine (SVM) according to some embodiments of the present invention can be used for classification purposes and/or for numeric prediction. A support vector machine for classification is referred to herein as "support vector classifier," support vector machine for numeric prediction is referred to herein as "support vector regression".

An SVM is typically characterized by a kernel function, the selection of which determines whether the resulting SVM provides classification, regression or other functions. Through application of the kernel function, the SVM maps input vectors into high dimensional feature space, in which a decision hyper-surface (also known as a separator) can be constructed to provide classification, regression or other decision functions. In the simplest case, the surface is a hyper-plane (also known as linear separator), but more complex separators are also contemplated and can be applied using kernel functions. The data points that define the hyper-surface are referred to as support vectors.

The support vector classifier selects a separator where the distance of the separator from the closest data points is as large as possible, thereby separating feature vector points associated with objects in a given class from feature vector points associated with objects outside the class. For support vector regression, a high-dimensional tube with a radius of acceptable error is constructed which minimizes the error of the data set while also maximizing the flatness of the associated curve or function. In other words, the tube is an envelope around the fit curve, defined by a collection of data points nearest the curve or surface.

An advantage of a support vector machine is that once the support vectors have been identified, the remaining observations can be removed from the calculations, thus greatly reducing the computational complexity of the problem. An SVM typically operates in two phases: a training phase and a testing phase. During the training phase, a set of support vectors is generated for use in executing the decision rule. During the testing phase, decisions are made using the decision rule. A support vector algorithm is a method for training an SVM. By execution of the algorithm, a training set of parameters is generated, including the support vectors that characterize the SVM. A representative example of a support vector algorithm suitable for the present embodiments includes, without limitation, sequential minimal optimization.

Regression techniques which may be used in accordance with the present invention include, but are not limited to linear Regression, Multiple Regression, logistic regression, probit regression, ordinal logistic regression ordinal Probit-Regression, Poisson Regression, negative binomial Regression, multinomial logistic Regression (MLR) and truncated regression.

A logistic regression or logit regression is a type of regression analysis used for predicting the outcome of a categorical dependent variable (a dependent variable that can take on a limited number of values, whose magnitudes are not meaningful but whose ordering of magnitudes may or may not be meaningful) based on one or more predictor variables. Logistic regressions also include a multinomial variant. The multinomial logistic regression model, is a regression model which generalizes logistic regression by allowing more than two discrete outcomes. That is, it is a model that is used to predict the probabilities of the different possible outcomes of a categorically distributed dependent variable, given a set of independent variables (which may be real-valued, binary-valued, categorical-valued, etc.).

A Bayesian network is a model that represents variables and conditional interdependencies between variables. In a Bayesian network variables are represented as nodes, and nodes may be connected to one another by one or more links. A link indicates a relationship between two nodes. Nodes typically have corresponding conditional probability tables that are used to determine the probability of a state of a node given the state of other nodes to which the node is connected. In some embodiments, a Bayes optimal classifier algorithm is employed to apply the maximum a posteriori hypothesis to a new record in order to predict the probability of its classification, as well as to calculate the probabilities from each of the other hypotheses obtained from a training set and to use these probabilities as weighting factors for future predictions. An algorithm suitable for a search for the best Bayesian network, includes, without limitation, global score metric-based algorithm. In an alternative approach to building the network, Markov blanket can be employed. The Markov blanket isolates a node from being affected by any node outside its boundary, which is composed of the node's parents, its children, and the parents of its children.

Instance-based algorithms generate a new model for each instance, instead of basing predictions on trees or networks generated (once) from a training set.

The term "instance", in the context of machine learning, refers to an example from a dataset.

Instance-based algorithms typically store the entire dataset in memory and build a model from a set of records similar to those being tested. This similarity can be evaluated, for example, through nearest-neighbor or locally weighted methods, e.g., using Euclidian distances. Once a set of records is selected, the final model may be built using several different algorithms, such as the naive Bayes.

Artificial neural networks are a class of algorithms based on a concept of inter-connected computer program objects referred to as neurons. In a typical artificial neural network, neurons contain data values, each of which affects the value of a connected neuron according to a pre-defined weight (also referred to as the "connection strength"), and whether the sum of connections to each particular neuron meets a pre-defined threshold. By determining proper connection strengths and threshold values (a process also referred to as training), an artificial neural network can achieve efficient recognition of image features. Oftentimes, these neurons are grouped into layers in order to make connections between groups more obvious and to each computation of values. Each layer of the network may have differing numbers of neurons, and these may or may not be related to particular qualities of the input data. An artificial neural network having a layered architecture belong to a class of machine learning procedure called "deep learning," and is referred to as deep neural network (DNN).

In one implementation, called a fully-connected DNN, each of the neurons in a particular layer is connected to and provides input value to those in the next layer. These input values are then summed and this sum is compared to a bias, or threshold. If the value exceeds the threshold for a particular neuron, that neuron then holds a value which can be used as input to neurons in the next layer of neurons. This computation continues through the various layers of the neural network, until it reaches a final layer. At this point, the output of the DNN can be read from the values in the final layer.

Unlike fully-connected DNNs, convolutional neural networks (CNNs) operate by associating an array of values with each neuron, rather than a single value. The transformation of a neuron value for the subsequent layer is generalized from multiplication to convolution. When the neural network is a CNN, the training process adjusts convolutional kernels and bias matrices of the CNN so as to produce an output that resembles as much as possible known image features.

The final result of the training of an artificial neural network having a layered architecture (e.g., DNN, CNN) is a network having an input layer, at least one, more preferably a plurality of, hidden layers, and an output layer, with a learn value assigned to each component (neuron, layer, kernel, etc.) of the network. The trained network receives an image at its input layer and provides information pertaining to images feature present in the image at its output layer.

The training of an artificial neural network includes feeding the network with training data, for example data obtained from a cohort of subjects. The training data include images which are annotated by previously identified image features, such as regions exhibiting pathology and regions identified as healthy. Based on the images and the annotation information the network assigns values to each component of the network, thereby providing a trained network. Following the training, a validation process may optionally and preferably be applied to the artificial neural network, by feeding validation data to the network. The validation data is typically of similar type as the training data, except that only the images are fed to the trained network, without feeding the annotation information. The annotation information is used for validation by comparing the output of the trained network to the previously identified image features.

In embodiments in which a trained machine learning procedure is employed, the procedure is fed with said the hyperspectral images. The trained machine learning procedure generates an output indicative of a likelihood that the hyperspectral images contains the hyperspectral signature of the substance.

The method can, in some embodiments of the present invention, continue to 17 at which the level of the biological substance (e.g., the amount of viruses or bacteria or fungi) in the sample is estimated. This can be done by a counting technique, whereby the number of identified occurrences of the identified hyperspectral signature in the hyperspectral images are counted and correlated to the level of the biological substance in the substance. In some embodiments of the present invention the estimation 17 comprises employing a linear function of the percentage of the occurrences of the identified hyperspectral signature within the hyperspectral image. Specifically, the estimation can be correlated to the quantity $\alpha F(p)+\beta$, where $\alpha$ and $\beta$ are updateable parameters, p is the percentage of the identified hyperspectral signature, and F is some function, optionally and preferably a linear function of p.

The percentage p is optionally and preferably defined relative to the total number of pixels in the hyperspectral image that for which the intensity is above a predetermined threshold. This ensures that the estimation is based on non-background pixels. The function F can be calculated based on the number of non-background pixels in the hyperspectral image or based on the energy represented by the non-background pixels in the hyperspectral image.

In some embodiments of the present invention F(p) is a linear function difference between the percentage of the identified hyperspectral signature and the percentage of the identified reference hyperspectral signature. The difference between these two percentages can, in some embodiments of the present invention be normalized, for example, by the percentage of the identified reference hyperspectral signature. A more detailed description of a preferred procedure for estimating the amount of the substance in the sample is provided in the Example section that follows.

The parameters $\alpha$ and $\beta$, and the parameters of the linear function F(p) are level estimation parameters that are used in 17 for estimating the level of the biological substance in the sample. At 18 the level estimation parameters are optionally and preferably updated using a machine learning procedure trained to generate an output of these parameters by analyzing the hyperspectral images obtained at 15 in comparison to previously obtained hyperspectral images.

The method ends at 19.

The detection of a biological substance in a sample 22 can be executed according to some embodiments of the present invention by system 20, as will now be explained with reference to FIG. 2.

Figure 2:
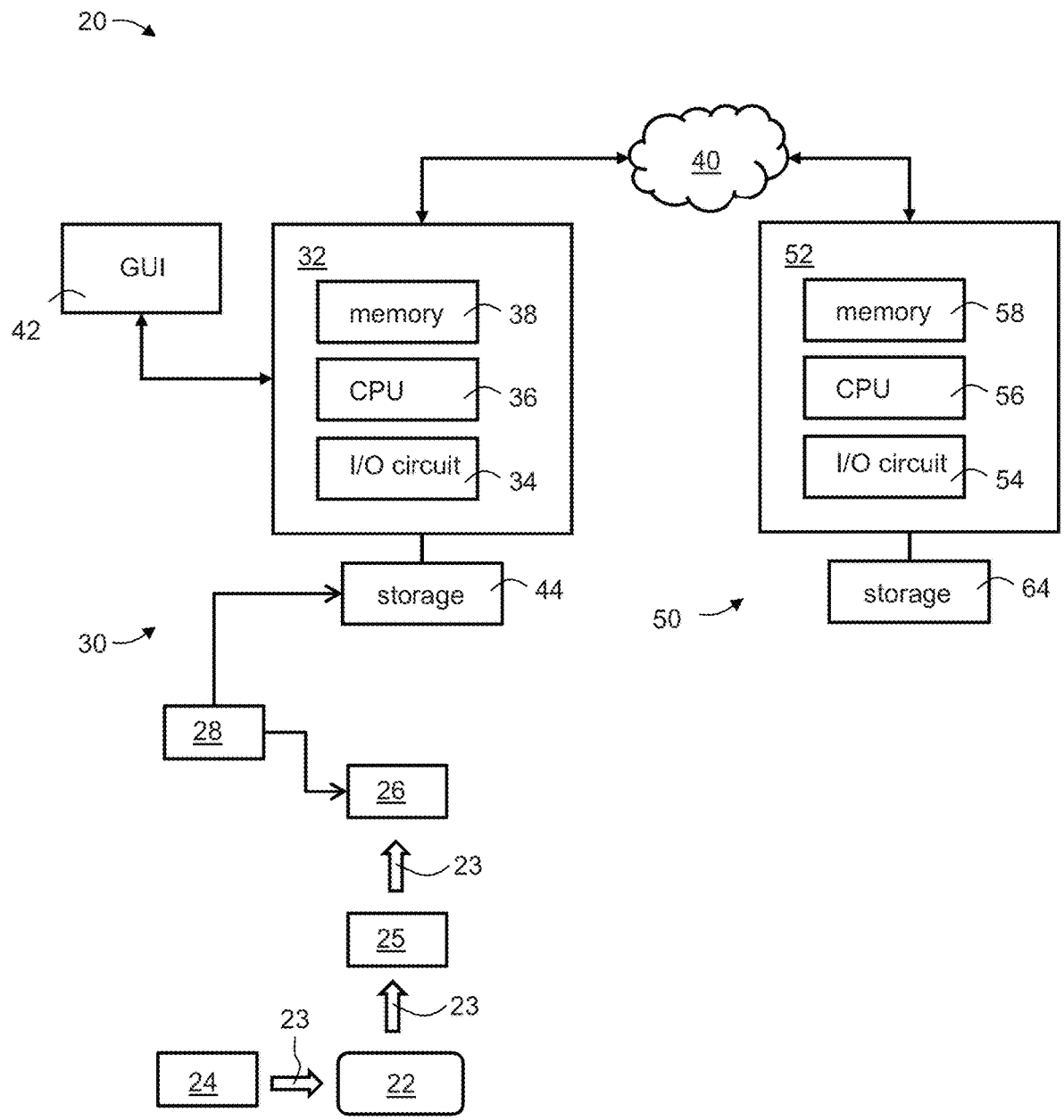
FIG. 2 is a schematic illustration of a system for detecting a biological substance in a sample, according to some embodiments of the present invention.

FIG. 2 illustrates a client computer 30 having a hardware processor 32, which typically comprises an input/output (I/O) circuit 34, a hardware central processing unit (CPU) 36 (e.g., a hardware microprocessor), and a hardware memory 38 which typically includes both volatile memory and non-volatile memory. CPU 36 is in communication with I/O circuit 34 and memory 38. Client computer 30 preferably comprises a user interface, e.g., a graphical user interface (GUI), 42 in communication with processor 32. I/O circuit 34 preferably communicates information in appropriately structured form to and from GUI 42.

GUI 42 and processor 32 can be integrated together within the same housing or they can be separate units communicating with each other. GUI 42 can optionally and preferably be part of a system including a dedicated CPU and I/O circuits (not shown) to allow GUI 42 to communicate with processor 32. Processor 32 issues to GUI 42 graphical and textual output generated by CPU 36. Processor 32 also receives from GUI 42 signals pertaining to control commands generated by GUI 42 in response to user input. GUI 42 can be of any type known in the art, such as, but not limited to, a keyboard and a display, a touch screen, and the like. In preferred embodiments, GUI 42 is a GUI of a mobile device such as a smartphone, a tablet, a smartwatch and the like. When GUI 42 is a GUI of a mobile device, the CPU circuit of the mobile device can serve as processor 32 and can execute the method optionally and preferably by executing code instructions.

A light source 24 illuminates the sample 22 by light 23 having a plurality of wavelength. Light source 24 can be a broadband light source, such as, but not limited to, a mercury lamp, or, alternatively, the light source 24 can be a laser light with a relatively narrow width (e.g., less than 50 nm or less than 40 nm or less than 30 nm, for example, 20 nm or less). A Fourier transform hyperspectral imaging system 26 images receives the light 23 after the interaction with the sample 22, optionally but not necessarily after the dispersion 25, and provide a hyperspectral image. Fourier transform hyperspectral imaging system 26 can be, for example, a fourier transform hyperspectral imaging system marketed under the trade name HyperEye® by Green Vision Systems Ltd., Tel Aviv, Israel.

A controller 28 controls hyperspectral imaging system 26 to acquire a plurality of hyperspectral images, and is also in communication with a non-transitory storage medium 44 of computer 30. Optionally and preferably, controller 28 also controls light source 24, for example, to perform wavelength scanning, and may also control a stage (not shown) carrying sample 22, for performing spatial scanning, is desired.

Storage medium 44 can also store computer code instructions for executing the method of the present embodiments, and processor 32 executes these code instructions. Storage medium 44 can also store one or more libraries of hyperspectral signatures as further detailed hereinabove. Storage medium 44 can alternatively or additionally store one or more trained machine learning procedures.

Storage medium 44 receives by means of controller 28 the hyperspectral images acquired by hyperspectral imaging system 26, and the code instructions stored on medium 44 can be run by loading them into the execution memory 38 of processor 32. In operation, processor 32 receives the hyperspectral images from storage 44 and use the library of hyperspectral signatures and/or the trained machine learning procedure stored on storage 44 to detect the biological substance in a sample.

Alternatively, part of the operations can be executed by a server computer 50. Server computer 50 can, similarly to computer 30, comprise a hardware processor 52, an I/O circuit 54, a hardware CPU 56, a hardware memory 58. I/O circuits 34 and 54 of client 30 and server 50 computers can operate as transceivers that communicate information with each other via a wired or wireless communication. For example, client 30 and server 50 computers can communicate via a network 40, such as a local area network (LAN), a wide area network (WAN) or the Internet. Server computer 50 can be in some embodiments be a part of a cloud computing resource of a cloud computing facility in communication with client computer 30 over the network 40.

Server 50 can further comprise one or more computer-readable storage media 64. Media 64 are preferably non-transitory storage media storing computer code instructions for executing the method of the present embodiments, and processor 52 executes these code instructions, by loading the code instructions into the execution memory 58. Storage media 64 preferably also store one or more libraries of hyperspectral signatures as further detailed hereinabove. Storage media 64 can alternatively or additionally store one or more trained machine learning procedures.

In embodiments in which server computer 50 is employed, processor 32 receives the hyperspectral images from storage 44 and typically transmits these images to server computer 50 over network 40. Server computer 50 can access media 64, and use the library of hyperspectral signatures and/or the trained machine learning procedure to detect the biological substance in a sample. Server computer 50 can also transmit to client computer 30 output pertaining to the detection of the biological substance, and client computer 30 can display this information on GUI 42.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Exemplified Protocol

Following is a description of an exemplified protocol for the detection of a biological substance suitable for the present embodiments.

(1) Sampling cycle:
  a. collect air bio-aerosols (e.g., particulate matter) using one or more air collectors; or
  b. using a sampler collect bio aerosol from a subject.

(2) Apply specific thermo-treatment to the sample with or without additional reagents to (i) enable to detect the specific bio-aerosols (e.g. Sars-Cov-2 viruses) and (ii) to reduce the dust background noise.

(3) Add one or more spectral markers to the sample, with or without additional reagent (to reduce the dust background noise).

(4) Place one or more drop(s) of the collected sample, mixed with the spectral markers and reagent, on a solid support, such as a filter, or a slide.

(5) With dedicated light sources scan the drop on the solid support in multi locations and acquire a plurality of hyperspectral images. Correlate the number of acquired images with the expected concentration of the biological substance. When the concentration is high, it is sufficient to acquire 10 hyperspectral images or less. When the concentration not high, acquisition of more hyperspectral images is preferred (e.g., more than 20 images, or more than 30 images). Different hyperspectral images are preferably acquired for different regions of the sample.

(6) Process the hyperspectral images:

a. apply background learning phase;

b. reduce the amount of background pixels from the matrix of the hyperspectral images;

c. compare the pixels of the hyperspectral images to the hyperspectral signatures of the library;

d. execute 6(a), 6(b) and 6(c) recursively several times for better probability of detection;

e. execute 6(a), 6(b) and 6(c) additionally on other samples;

(7) Analysis the results of (6) to generate qualifying and quantifying data per cycle (for example, existence of the substance, certainty of the results, detected anomalies, etc.).

(8) Clean the air inlets and pipes and sample holders or filter roller using both optical heaters, UV and Ions generators.

Exemplified Estimation of the Level of the Biolonical Substance in the Sample The total number of pixels of the hyperspectral image for which the intensity is above a predetermined threshold is referred to herein as the number of non-background pixels, and denoted TotalArea.

The total energy represented by all the non-background pixels is denoted TotalEng.

The percentage of the number pixels for which a hyperspectral signature of the biological substance is identified, relative to the number of non-background pixels is denoted PST %.

The percentage of the number pixels for which a reference hyperspectral signature is identified, relative to the number of non-background pixels is denoted NGT %.

According to some embodiments of the present invention the method calculates an area-related quantity, referred to a FeatureI, and being defined as:

$$FeatureI = \frac{NormPST - NormNGT}{NormNGT} \cdot A1 + B1$$

where, A1 and B1 are updatable parameters, and where NormPST and NormNGT are, respectively, the percentages PST % and NGT %, multiplied by the number of non-background pixels, and normalized by a predetermined average area parameter TotalAreaAvrg. Specifically:

$$NormPST = \frac{PST\ \%}{TotalAreaAvrg} \cdot TotalArea$$

$$NormNGT = \frac{NGT\ \%}{TotalAreaAvrg} \cdot TotalArea$$

In experiments performed by the inventors A1 was set to about 10, B1 was set to about 5, and TotalAreaAvrg was set to about 0.3. Preferably the predetermined average area parameter TotalAreaAvrg is re-calculated after each cycle of measurements by averaging the values of TotalArea across the cycles.

In some embodiments of the present invention the method calculates an energy-related quantity referred to a FeatureII. FeatureII can be calculated similarly to FeatureI except that instead of multiplying the percentages PST % and NGT % by the number of non-background pixels, they are multiplied by TotalEng, and instead of normalized them by the average area parameter TotalAreaAvrg, they are normalized them by a predetermined average energy parameter TotalEngAvrg. Specifically:

$$FeatureII = \frac{NormPSTEng - NormNGTEng}{NormNGTEng} \cdot A2 + B2$$

where A2 and B2 are updatable parameters, $$NormPSTEng = \frac{PST\ \%}{TotalEngAvrg} \cdot TotalEng$$

and $$NormNGTEng = \frac{NGT\ \%}{TotalEngAvrg} \cdot TotalEng$$

In experiments performed by the inventors A2 was set to about 8.5, B2 was set to about 6.2, and TotalEngAvrg was set to about 3.8. Preferably the predetermined average energy parameter TotalEngAvrg is re-calculated after each cycle of measurements by averaging the values of TotalEng across the cycles.

Experimental

M13KO7 Phages

M13KO7 phages were tested at different concentrations and scenarios. In this set of experiments, excellent detection abilities, with limit of detection of less than 1000 phages and very low SNR, were demonstrated. The HyperEye®-AP[ID] station of Green Vision Systems Ltd was used as the light source and hyperspectral imaging system. Three measurement cycles were performed. In each cycle eight samples, denoted A through H, were tested. The numbers of viruses in 4 microliters of sample are listed in Table 1, below and the detected values from the HyperEye®-AP [ID] are listed in Table 2, below.

TABLE 1

| Sample | Viruses in 4 microliter |
| --- | --- |
| A | 26,000 |
| B | 13,000 |
| C | 6600 |
| D | 3300 |
| E | 1650 |
| F | 835 |
| G | 412 |
| H | 0 |

TABLE 2

| Sample | Viruses per 8 microliter |
| --- | --- |
| A | 5 |
| B | 2.3 |
| C | 1.6 |
| D | |
| E | 0.55 |
| F | |
| G | 0.27 |
| H | No viruses 0.06 |

Figure 3A:
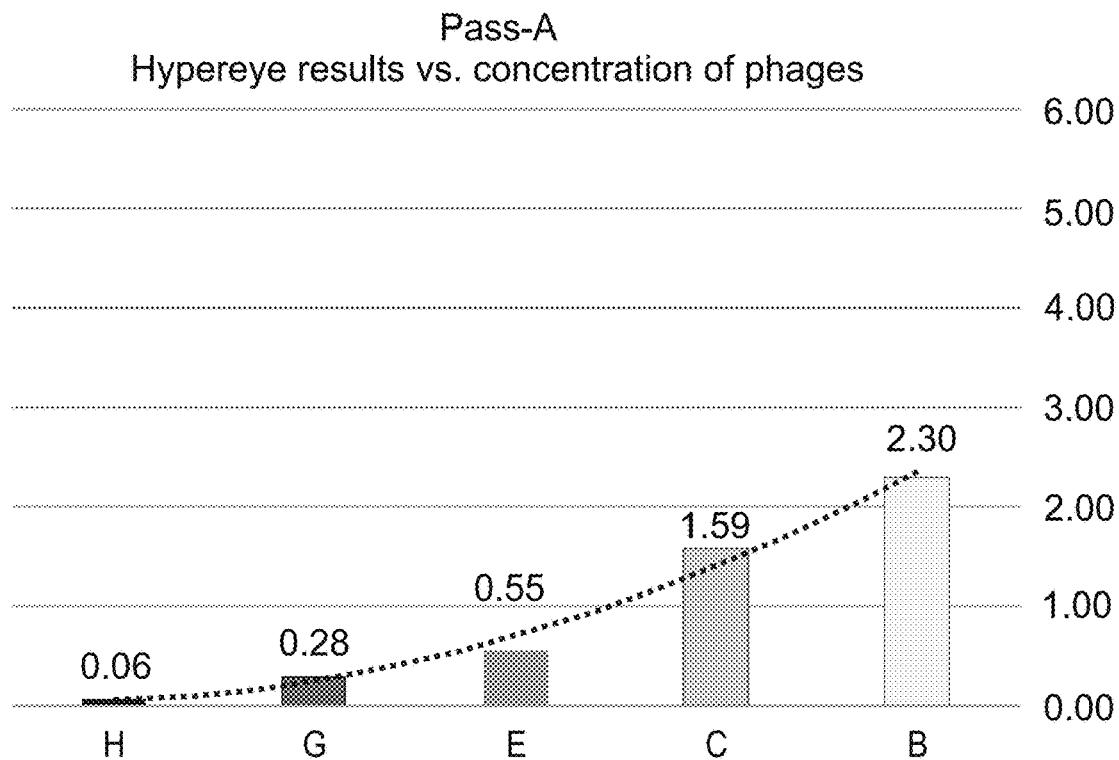
FIGS. 3A-C show results obtained in experiments performed according to some embodiments of the present invention for the detection of M13KO7 phages.
Figure 3B:
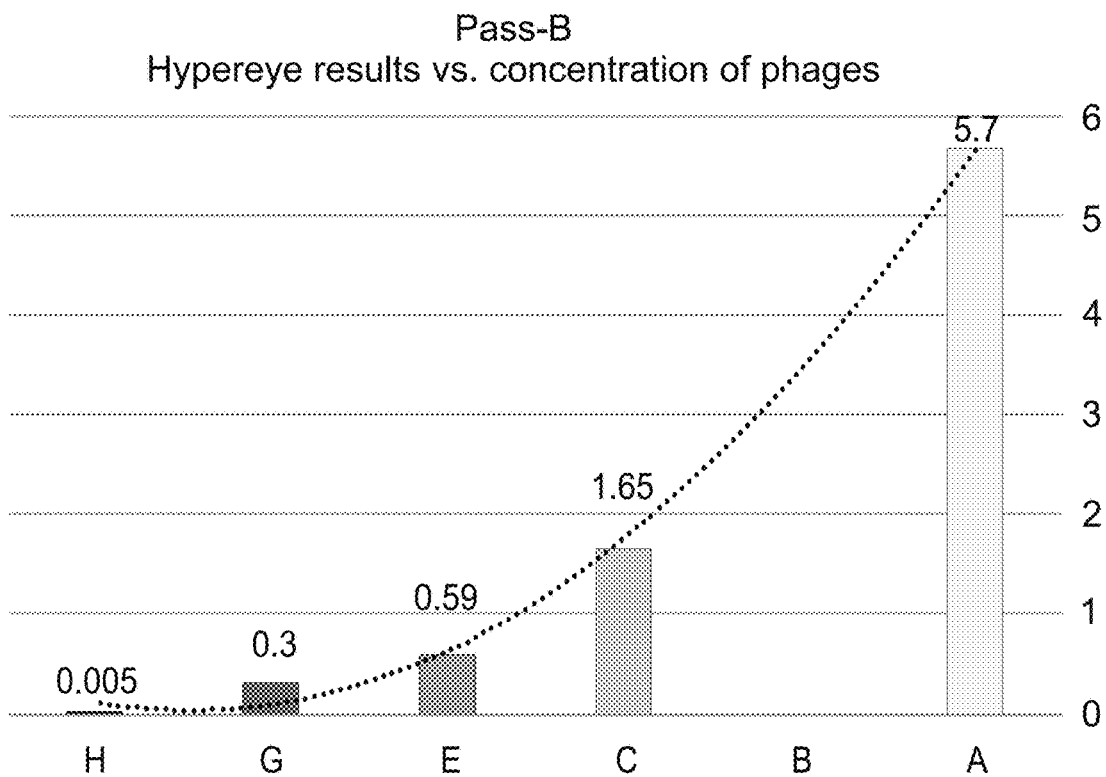
Figure 3C:
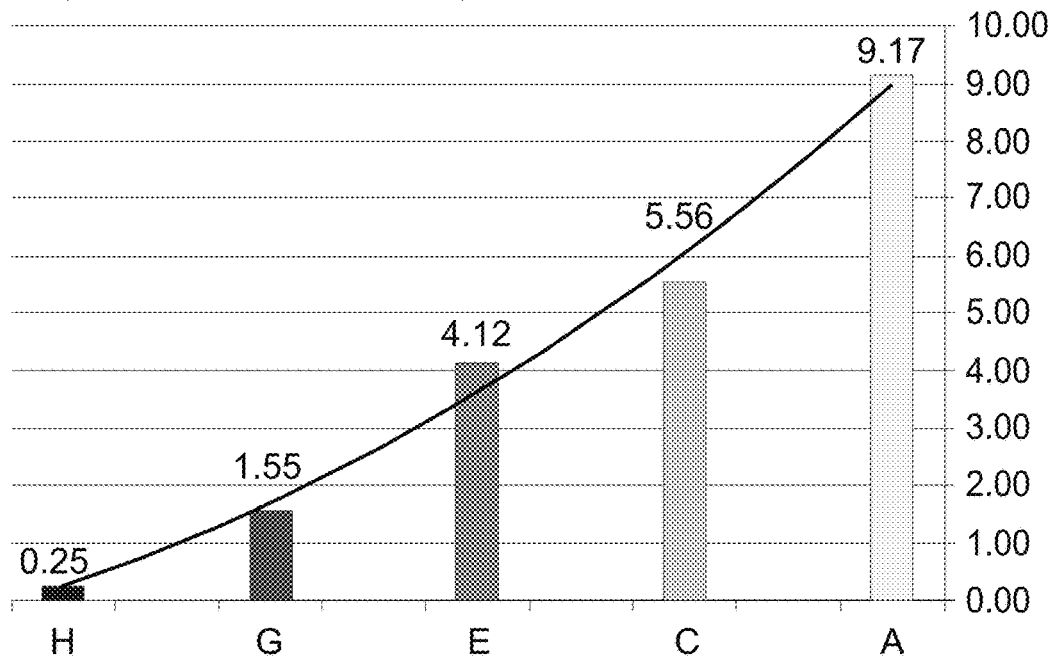

FIGS. 3A-C show the results obtained versus the concentration of the phages, for each of the three cycles. FIGS. 3A-C demonstrate that the technique of the present embodiments is capable of identifying viruses at different concentrations with high Probability of Detection (POD): the detection limit, samples with no phases, is value of 0.05 vs. 0.27 at low concentration of 400 phases per one small drop, with over 5 times value above background, meaning that the POD is over 95%. FIGS. 3A-C also demonstrate high sensitivity: detection of less than 200 viruses is observed, with detection value of 0.25 at G concentration of 450 phases per small drop and with limit of detection of 0.1 reduction of factor two on the detected value enables detecting samples with about 200 phases per drop. FIGS. 3A-C also demonstrate high SNR (above $2^{0.27/0.06}$). This high SNR enables the aforementioned high POD. FIGS. 3A-C also demonstrate low False Alarm Rate: the threshold is much lower that the low value of detection limit needed over 400 phages, taken more images per cycle will improve the POD. Each cycle took under 15 minutes to complete.

Lentiviruses, Pseudo Types with SARS-CoV

Lentiviruses were tested at different concentrations and scenarios. The HyperEye®-AP[ID] station of Green Vision Systems Ltd was used as the light source and hyperspectral imaging system. Two measurement cycles were performed. The results are shown in FIGS. 4A and 4B and Table 3.

TABLE 3

| Different Concentration | one drop - 4 μl |
|---|---|
| A | $4 \cdot 10^3$ viruses/ml |
| B | $2 \cdot 10^3$ viruses/ml |
| C | $1 \cdot 10^3$ viruses/ml |
| D | $0.5 \cdot 10^3$ viruses/ml |
| E, Background | no viruses |

Figure 4A:
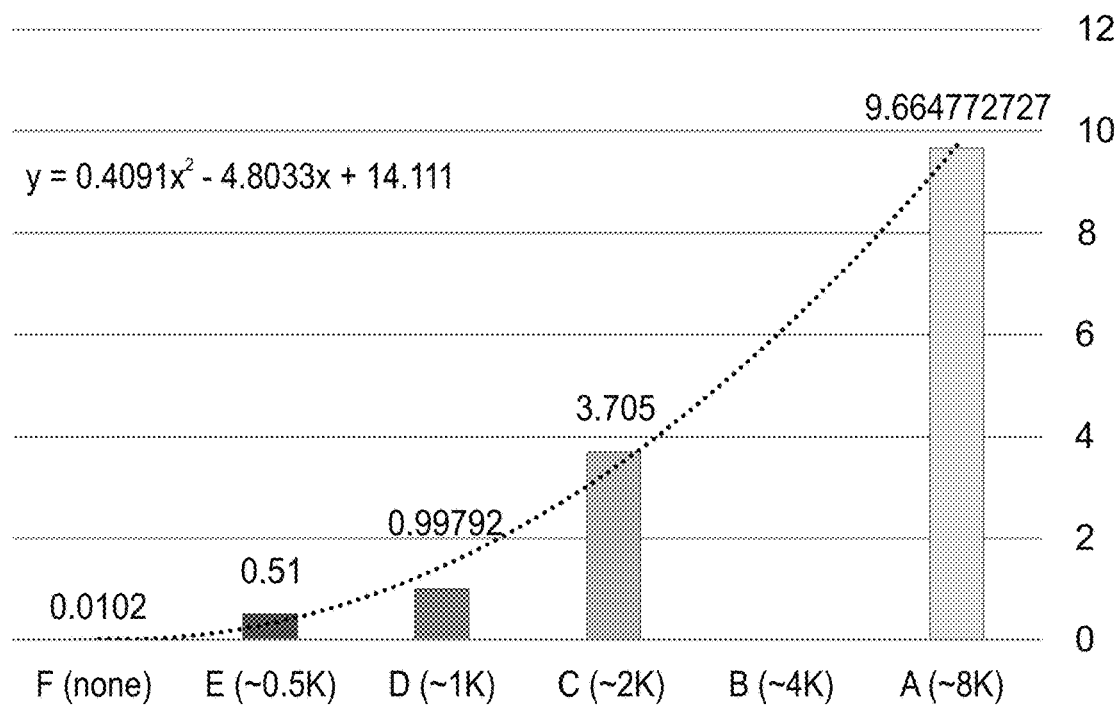
FIGS. 4A and 4B show results obtained in experiments performed according to some embodiments of the present invention for the detection of lentiviruses.
Figure 4B:
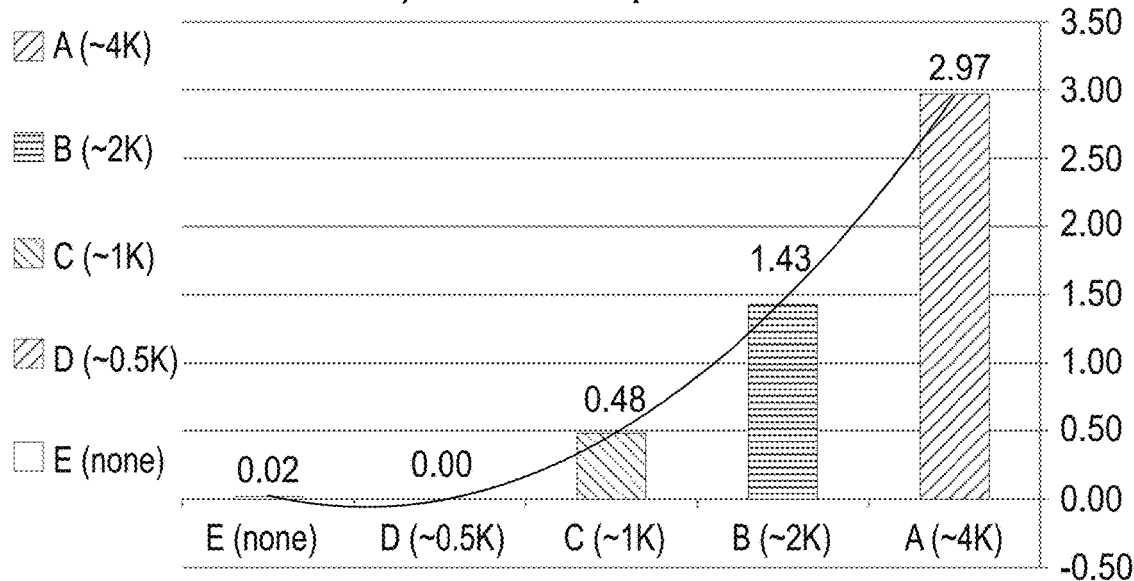

FIGS. 4A and 4B demonstrate that the technique of the present embodiments is capable of identifying lentivirus at low level of concentration down to 400 viruses per drop (see sample E) with high Probability of Detection (more than 95%): the value of 0.51 at 500 viruses per drop vs. 0.01 of drop with no virtues provides SNR of over 25 (25:1) times more signal vs. background. The detection limit of 0.1 provides low False Alarm Rate with high performances of over 95% of the times detecting sample with viruses at concentration of over 2500 viruses per cycle. In addition, high sensitivity (detection of less than 100 viruses) is observed: as the SNR is above 25, the ability to detect less than 100 viruses is 5 times less over 25 times of signal vs. background values), and with the high SNR (25:1) $2^{0.5/0.01} \gg 25$ see results of G vs. F in FIG. 4A]] the average values of no viruses was 0.01 and the E sample provide a results value of 0.5, at 500 viruses per drop. Further low False Alarm Rate (less than 1:100) was observed: with very high SNR the detection limit can be set at high value (e.g. 0.05) yet far from the signal detection limit (e.g. 0.25), this demonstrates that above 250 ($10*2^{0.25/0.01} > 250$) times of cycles per one fault cycle. Each cycle took under 15 minutes to complete.

SARS-CoV-2 Clinical Samples

SARS-CoV-2 saliva samples collected from hospital personnel were tested at different concentrations and scenarios. The HyperEye®-AP [ID] station of Green Vision Systems Ltd was used as the light source and hyperspectral imaging system. For personnel sampling, samples were collected using a standard set of swabs, and using saliva sample kits including tubes and pipettes to transfer samples from the subject to a test tube (that includes the reagent (mixed on antibodies and two markers. For indoor airborne sampling, air was collected on a filter with controlled air pump (pumping rate of from about 5 liters per min to about 100 litter per min or more) from the tested area and, after X or more minutes of air collection (X=30, 60, 120, 240, 600), the reagent was added to the filter and then scanned for data retrieval and analysis.

Two measurement cycles were performed for each sample to confirm the robustness of the results and check the time between sampling. Nine samples, denoted S1 through S9 were analyzed. Samples S1, S2, S3 were negative, samples S4, S5, S6, S7, S8, S9 were positive. The first measurement cycle was performed at the same day the samples were collected, and the second measurement cycle was performed 3 days after the samples were collected. Samples were stored at 4° C.

Table 4 summarizes the collected data and the results of the experiments.

TABLE 4

| Code No. | Saliva samples | PCR CT | FeatureI $R^2 = 0.7$ | FeatureII HyperEye Results |
|---|---|---|---|---|
| S1 | 293-sal | Negative | Negative | 0.000 ; Negative |
| S2 | 293-sal | Negative | Negative | 0.001; Negative |
| S3 | 293-sal | 36.68 | 34.70 | 0.12, Low -might be ill. |
| S4 | 293-sal | Negative | Negative | 0.000; Negative |
| S5 | 293-sal | Negative | Negative | 0.004; Negative |
| S6 | 293-sal | Negative | Negative | 0.012; Negative |
| S7 | 293-sal | 31.8 | 31.446 | Positive, low dose |
| S8 | 293-sal | 30.8 | 31.501 | Positive, low dose |
| S9 | 293-sal | 29.47 | 30.178 | Positive, low/medium dose |
| S10 | 293-sal | No data | | Positive, low dose |
| S12 | 293-sal | 16.18 | 16.158 | Positive, high dose |
| S14 | 293-sal | 32.33 | 30.356 | Positive, low/medium dose |
| S15 | 293-sal | 37.83 | 32.496 | Positive, low dose |
| S16 | 293-sal | 30.34 | 33.726 | Positive, low/medium dose |
| S17 | 293-sal | 25 | 30.632 | Positive, medium + dose |
| S18 | 293-sal | 21.64 | 20.841 | Positive, high |

Figure 5A:
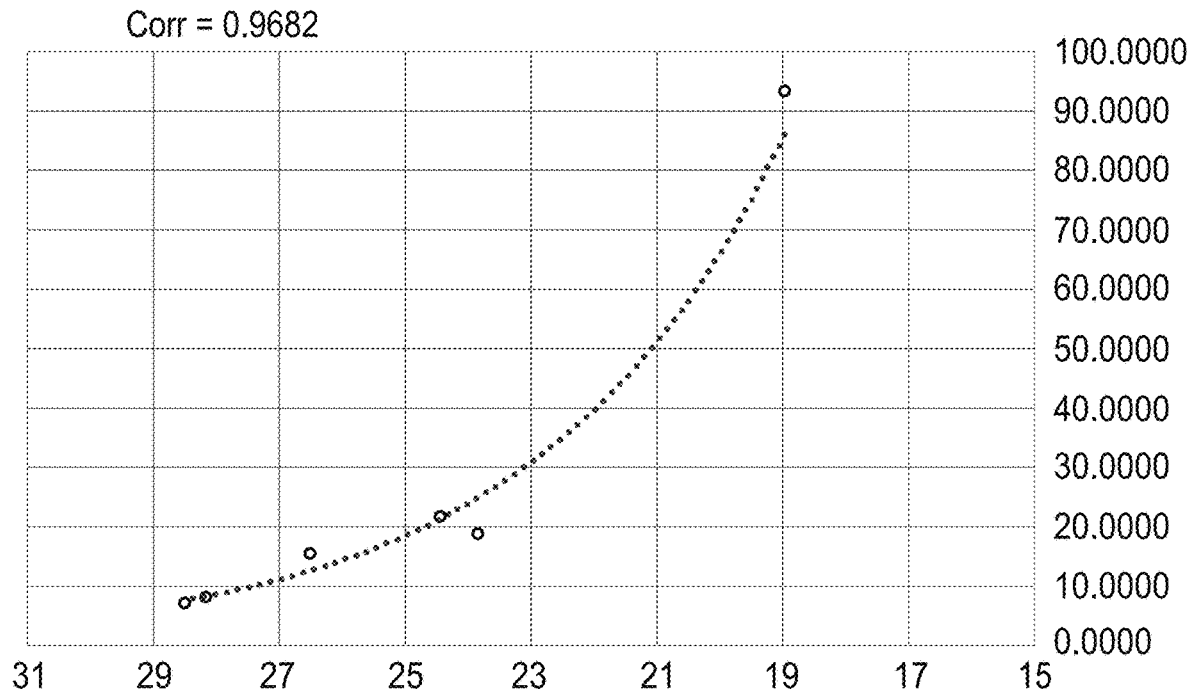
FIGS. 5A and 5B show results obtained in experiments performed according to some embodiments of the present invention for the detection of SARS-CoV-2 from saliva samples of 9 subjects.
Figure 5B:
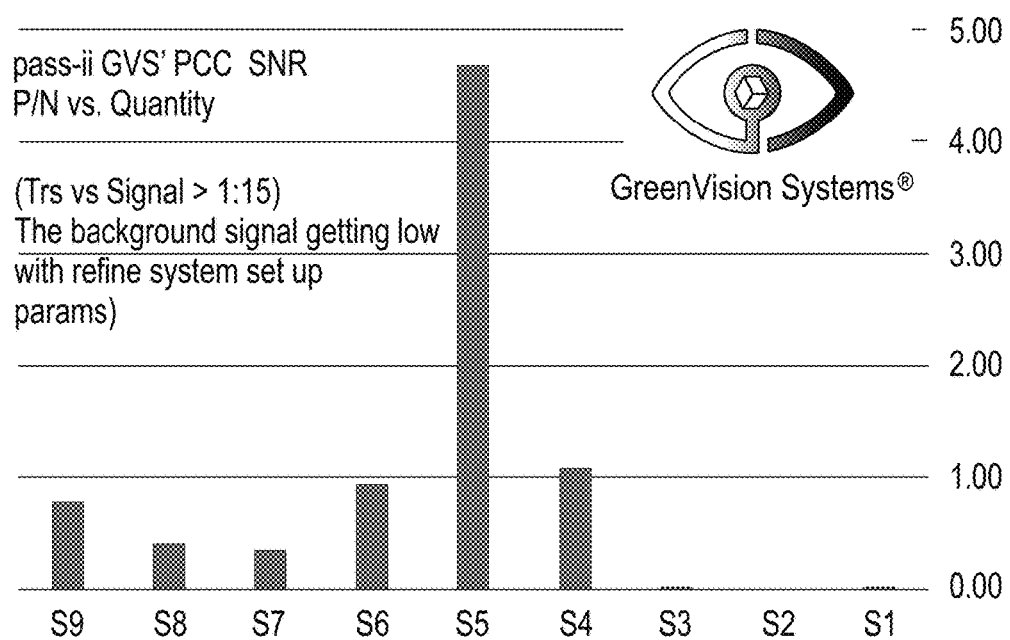

FIG. 5A is a graph showing the results obtained by hyperspectral imaging according to embodiments of the present invention vs. results obtained by PCR, and FIG. 5B is a bar chart showing the values of the features defined above. As shown for subject Nos. S1-S3 (samples with Negative, not infected, samples PCR' results), the value is substantially small and for subject Nos. S4-S9 (samples with positive, infected, samples PCR' results) the value is high, demonstrating that the features calculated according to some embodiments of the present invention correlate well with the PCR results.

Additional tests were conducted for 14 hospital personnel who provided saliva and lung samples. Table 5 summarizes the collected data and the results of the experiments.

TABLE 5

| Sample of personnel code number | Code | PCR CT Labs | HyperEye (Saliva) | Sample of personnel code number | Code | HyperEye (lung) |
|---|---|---|---|---|---|---|
| Sal-1 | 298-sal | 21.47 | 21.330 | Nas-1 | 298-Nas | 21.574 |
| Sal-2 | 298-sal | 22.69 | 24.230 | Nas-2 | 298-Nas | 23.262 |
| Sal-6 | 298-sal | 27.74 | 28.074 | Nas-6 | 298-Nas | 30.843 |
| Sal-7 | 298-sal | 28.49 | 27.078 | Nas-7 | 298-Nas | 26.970 |
| Sal-8 | 298-sal | 28.65 | 30.108 | Nas-8 | 298-Nas | 29.304 |
| Sal-10 | 298-sal | 29.42 | 29.419 | Nas-10 | 298-Nas | 31.012 |
| Sal-11 | 298-sal | 29.99 | 31.943 | Nas-11 | 298-Nas | 28.599 |
| Sal-12 | 298-sal | 30.58 | 29.136 | Nas-12 | 298-Nas | 30.704 |
| Sal-14 | 298-sal | 31.54 | 33.095 | Nas-14 | 298-Nas | 32.179 |
| Sal-16 | 298-sal | 31.65 | 32.461 | Nas-16 | 298-Nas | 30.845 |
| Sal-17 | 298-sal | 32.02 | 31.793 | Nas-17 | 298-Nas | 31.169 |
| Sal-18 | 298-sal | 32.25 | 30.515 | Nas-18 | 298-Nas | 32.279 |

TABLE 5-continued

| Sample of personnel code number | Code | PCR CT Labs | HyperEye (Saliva) | Sample of personnel code number | Code | HyperEye (lung) |
|---|---|---|---|---|---|---|
| Sal-19 | 298-sal | 33.74 | 32.051 | Nas-19 | 298-Nas | 32.205 |
| Sal-20 | 298-sal | 33.93 | 32.878 | Nas-20 | 298-Nas | 33.507 |

Figure 6A:
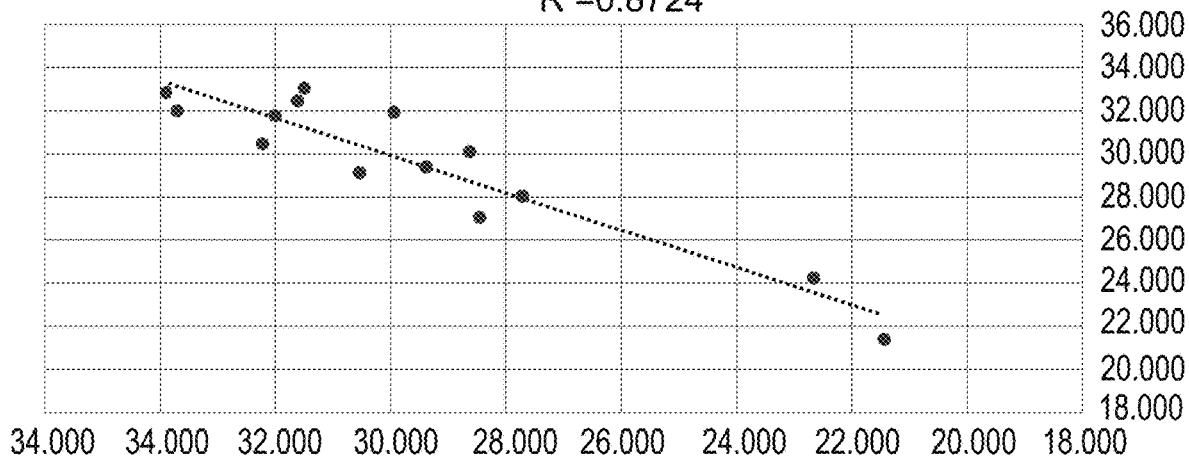
FIGS. 6A and 6B show results obtained in experiments performed according to some embodiments of the present invention for the detection of SARS-CoV-2 from saliva and lung samples of 14 subjects.
Figures 6B, 7A, 7B:
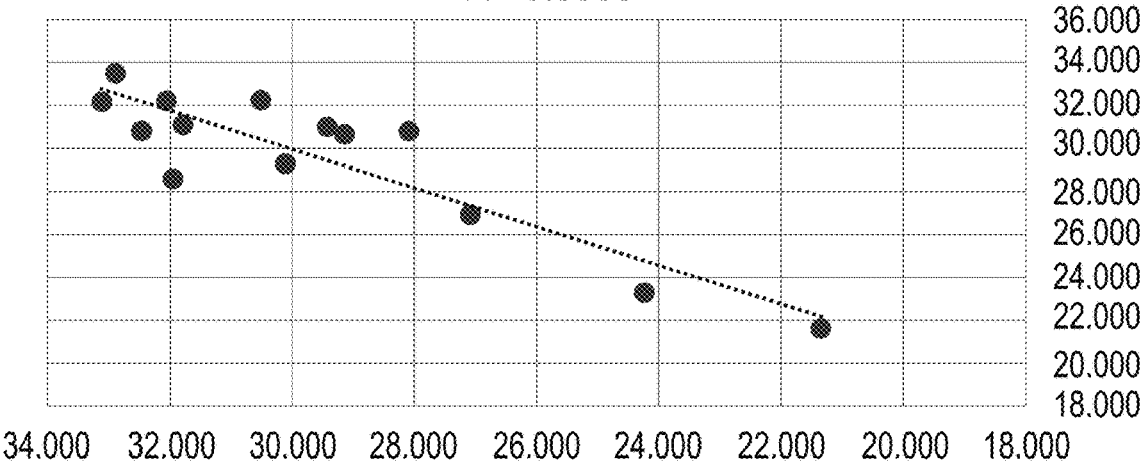
FIGS. 7A and 7B are representative examples of hyperspectral images of saliva samples obtained from a subject found to be negative to SARS-CoV-2 (FIG. 7A), and from a subject found to be positive to SARS-CoV-2 (FIG. 7B), where both images were acquired using the same protocol.

FIG. 6A shows results of RT-PCR vs. the technology of the present embodiments, after a first cycle of calibration. Correlation between the two methods demonstrate high performance. FIG. 6B shows comparison between results obtained using the hyperspectral imaging of the present embodiments for saliva samples and results obtained using the hyperspectral imaging of the present embodiments for lung samples. High correlation (R≈0.9) was observed, demonstration that the technique of the present embodiments can provides reliable results both for saliva samples and for gold standard lung samples.

Representative examples of hyperspectral images of saliva samples obtained from a subject found to be negative to SARS-CoV-2, and from a subject found to be positive to SARS-CoV-2 are shown in FIGS. 7A (negative) and 7B (positive). Both images were acquired using the same protocol. FIGS. 7A-B demonstrate the ability of the Fourier transform hyperspectral imaging of the present embodiments to reliable diagnose subject with SARS-CoV-2.

The experimental results presented in this Example demonstrates that the hyperspectral imaging technology of the present embodiments can detect, trigger and/or determine SARS-CoV-2, also other viruses, exist in different media. Can also check massive personnel taken both bio-aerosols from human body and the, much easier and safe to obtain, saliva samples.

The experimental results presented in this Example demonstrates that the hyperspectral imaging technology of the present embodiments can check massive personnel taken both bio-aerosols from human body and the, much easier and safe to obtain, saliva samples.

The hyperspectral imaging technology of the present embodiments can loads at each test cycle tens of personnel's samples, due to high sensitivity capabilities.

The experimental results presented in this Example demonstrates that the hyperspectral imaging technology of the present embodiments can detect and classifying existent of viruses in human samples saliva's and bio aerosols from breaths.

The experimental results presented in this Example demonstrates that the hyperspectral imaging technology of the present embodiments can operate in near real-time for on sites technologies, for indoor and outdoor detection of viruses such as, but not limited to, SARS-CoV-2.

The hyperspectral imaging technology of the present embodiments can detect and trigger on infected personnel's looking on more than one biological substance (e.g. coronavirus).

The experimental results presented in this Example demonstrates that the hyperspectral imaging technology of the present embodiments provides results that are well-correlates to the RT-PCR lab systems methodologies. Since this is a biochemical imaging microscopic-based approach that does not require any further laboratory or data analyses, the detection and source contributions can be determined in near-real time (i.e., less than 10 minutes from sample collection).

To test the precision of the identification, the experiments described in this Example included repetitive scans on different sections of the same solid support and resulted in source attribution results less than or equal to +/−10%.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of detecting a biological substance in a sample, the method comprising:
   collecting the sample as an aerosol;

adding to the sample a bio-marker that directly or indirectly binds to the biological substance in the sample;

illuminating the sample by light;

at a hyperspectral imaging system, imaging the illuminated sample by Fourier transform hyperspectral imaging a plurality of times, to generate a plurality of hyperspectral images;

accessing a computer readable medium containing a library of hyperspectral signatures of bio-markers;

at an image processor, analyzing said plurality of hyperspectral images using said library to detect the biological substance in the sample by identifying hyperspectral signatures in said plurality of hyperspectral images and comparing said identified hyperspectral signatures to hyperspectral signatures of bio-markers in said library; and estimating a level of the identified biological substance in the sample, using a linear function of a percentage of occurrences of the identified hyperspectral signature within the hyperspectral image, wherein for each hyperspectral image of said plurality of hyperspectral images said linear function is calculated based on a difference between a normalized percentage of pixels identified as a hyperspectral signature and a normalized percentage of pixels identified as a reference hyperspectral signature in a reference hyperspectral image, wherein said percentage of pixels identified as said hyperspectral signature is relative to a number of non-background pixels in said hyperspectral image, wherein said percentage of pixels identified as a reference hyperspectral signature in said reference hyperspectral image is relative to a number of non-background pixels in said reference hyperspectral image, and wherein said non-background pixels are pixels for which an intensity is above a predetermined intensity threshold.

2. The method according to claim 1, comprising adding to the sample a bio-marker that directly or indirectly binds to said substance, wherein said library comprises hyperspectral signatures of said bio-markers.

3. The method according to claim 1, wherein said collecting is from a mammalian subject.

4. The method according to claim 1, comprising collecting the sample from a plant.

5. The method according to claim 1, comprising applying a thermal treatment to the sample prior to said imaging.

6. The method according to claim 1, wherein said hyperspectral imaging system includes a microscope, and wherein said substance is a virus.

7. The method according to claim 6, wherein said virus is an airborne virus.

8. The method according to claim 1, wherein said substance is a fungus.

9. The method according to claim 1, wherein said hyperspectral imaging system includes a microscope, and wherein said substance is a bacterium.

10. The method according to claim 1, wherein at least one of said hyperspectral signatures in said library comprises a hyperspectral image.

11. The method according to claim 1, wherein said illuminating includes illuminating the sample by light from at least two different directions simultaneously.

12. The method according to claim 1, wherein said plurality of hyperspectral images of the sample are acquired from two different viewpoints with respect to the entire sample.

13. The method according to claim 1, wherein said illuminating includes illuminating the sample by one of at least one broadband light source and a light source having a width of less than 20 nm.

* * * * *